United States Patent [19]

Shaw

[11] Patent Number: 5,008,082
[45] Date of Patent: Apr. 16, 1991

[54] ANALYZERS USING LINEAR SAMPLE TRAYS WITH RANDOM ACCESS

[75] Inventor: James D. Shaw, Hilton, N.Y.
[73] Assignee: Eastman Kodak Company, Rochester, N.Y.
[21] Appl. No.: 236,588
[22] Filed: Aug. 25, 1988
[51] Int. Cl.[5] .................... G01N 35/02; G01N 35/04; G01N 35/06
[52] U.S. Cl. ........................ 422/65; 422/63; 422/67; 422/68.1; 422/100; 436/43; 436/47; 436/48; 436/49
[58] Field of Search ............. 422/58, 63, 64, 65, 422/67, 68.1; 436/43, 47, 48, 49; 356/39, 244, 246

[56] References Cited

U.S. PATENT DOCUMENTS

| | | | |
|---|---|---|---|
| 3,544,272 | 12/1970 | Vaills | 422/65 |
| 3,897,216 | 7/1975 | Jones | 422/104 |
| 4,058,367 | 11/1977 | Gilford | 422/67 |
| 4,113,436 | 9/1978 | Werder et al. | 422/65 |
| 4,115,861 | 9/1978 | Allington | 422/65 |
| 4,287,155 | 9/1981 | Tersteeg et al. | 422/64 |
| 4,452,899 | 6/1984 | Alston | 422/63 |
| 4,483,927 | 11/1984 | Takekawa | 422/65 |
| 4,678,752 | 7/1987 | Thorne et al. | 422/65 |
| 4,727,033 | 2/1988 | Hijikata et al. | 422/65 |
| 4,812,392 | 3/1989 | Miyake et al. | 422/65 |
| 4,855,109 | 8/1989 | Muraishi et al. | 422/63 |
| 4,927,765 | 5/1990 | Saxon et al. | 422/63 |

Primary Examiner—David L. Lacey
Assistant Examiner—Kimberly A. Trautman
Attorney, Agent, or Firm—Dana M. Schmidt

[57] ABSTRACT

An analyzer and sample trays are disclosed which permit more random sampling of patient samples than is conventional. The trays are open at the sides, and preferably include flags for sensing, and structure on the bottom wall for releasably engaging a conveyor. The analyzer provides a separate linear track for each of the trays, in which the trays are mounted, and another conveyor for reciprocating each of the trays within its respective track and to a position that intersects a path taken by a moving aspirating and dispensing station.

11 Claims, 7 Drawing Sheets

ANALYZERS USING LINEAR SAMPLE TRAYS WITH RANDOM ACCESS

FIELD OF THE INVENTION

This invention relates to analyzers for liquid analytes, and more specifically to means for supplying patient sample to such analyzers.

BACKGROUND OF THE INVENTION

Analyzers conventionally require that patient sample be brought into operative association, such as by aspiration and dispensing, with test reagents, which can be in a dried test element. This operative association usually is called a metering operation. If dispoable tips are used for the aspiration and dispensing, those tips are a further component that needs to be brought to the metering operation. The key component to the metering operation is aspirating and dispensing means, such as an automated pipette connected to means for evacuating and pressuring the pipette in alternating sequences.

One method of bringing the disposable tips, patient sample, and test elements "to " the pipette station is shown in U.S. Pat. No. 4,287,155, especially FIG. 3. In such an arrangement, the sample is transferred to open containers that are arranged on a rotating turntable (which may have four segements) in an arc. In another arc at a different radius on that turntable are placed disposable tips, so that the pipette first traverses to a position above the tips, lowers to pick up a tip, rises back to a traverse position, traverses to a position above the open sample containers, and lowers for aspiration. Thereafter the pipette traverses to another location to dispense sample onto a test element.

Such an arrangement has been very effective in analyzers that have been outstanding in the field of clinical chemistry. There are some aspects, however, which can be further improved. One of these is that the rotating turntable necessarily occupies much more volume than just that taken up by the arcuate arrangement of sample containers or of disposable tips. Therefore, the turntable is not very space-efficient nor does it allow for *other* turntables to be closely associated therewith. Another aspect for improvement is that each turntable necessarily limits its usefulness to there being an adequate number of disposable tips present for each sample container. If this is not the case, the analyzer sequence must be interrupted to provide extra tips, and such tips can be supplied *only* while an interrupt is in effect.

Still another area of improvement is to provide an analyzer that will allow STAT samples to be taken out of turn. Patient samples taken sequentially off a rotating turntable do not readily provide such a capability. Because of that, the prior turntable arrangement has induced operators to attempt to manually insert STAT samples in the turntable "close to" the position being aspirated. This not only creates a hazard to the operator but it can interfere with the automatic operation of the analyzer, particularly if the manual insertion fails in any respect.

Therefore, there has been a need prior to this invention to provide an analyzer with sample supply means that are more efficient in their use of space; accommodate additional, separately loadable sample supply means side-by-side; are independent of the supply of disposable tips; and/or allow for more random sampling of containers.

There have been some attempts at compacting trays of patient sample into linear arrays, so that a tray can be fed past a bar code reader to a metering station. For example, U.S. Pat. No. 4,727,033 teaches such an arrangement, using trays or racks 22, FIG. 2. However, in this arrangement, there is only one linear track (track 25) that is disposed to intersect the path of traverse of the metering pipette 32. As a result, the trays have to be mounted for movement into and out of the track 25 position. This in turn means that each tray is tied to, or in series with, the other trays, all in a track 20 that runs perpendicular to track 25. Thus, not only do all the trays have to be conveyed in a direction other than the operative one that intersects the metering pipette, but in addition there is no provision for removal of a tray from the sequence, until the tray reaches the end of track 20. There is no recognition in that patent that trays would benefit from being independently operable, such as would occur if each tray had its own separate track. That is, an individual tray containing a STAT sample cannot be taken out of order since the trays can be fed to track 25 only one at a time, in order. Furthermore, no provision is made to provide the pipette with disposable tips of any kind, let alone in a way that renders the supply of tips independent from the supply of patient sample.

SUMMARY OF THE INVENTION

I have designed an analyzer and tray therefor which provide the desired improvements noted above.

More specifically, in one aspect of the invention there is provided an analyzer comprising first supply means for supplying patient sample, aspirating and dispensing means for aspirating sample from the supply means and dispensing sample onto a test element, second supply means for supplying disposable tips for the aspirating means, third supply means for supplying test elements, and means for moving the aspirating and dispensing means in the analyzer relative to the first, second and third supply means along a predetermined path and into operative association with the sample, a disposable tip and a test element, respectively. The analyzer is improved in that the first supply means comprise (a) a plurality of trays each comprising means for holding a plurality of sample containers in a linear array, (b) a separate linear track for each of the trays, in which the trays are mounted, and (c) means for reciprocating each of the trays within its respective track and to a position that intersects the path of the aspirating and dispensing means.

In another aspect of the invention there is provided a tray for containers to be placed in an analyzer, such tray comprising means for holding a plurality of containers upright in a linear array, the means comprising two opposed vertical side walls providing as a major dimension of the tray, its length; a bottom wall and end walls connecting the side walls, both of the side walls having more than fifty percent of their surface removed so as to provide an access to the containers, a flag on the container to identify it to a sensor in an analyzer, and means in the undersurface of the bottom wall, for releasibly engaging a conveyor belt.

Thus, it is an advantageous feature of the invention that an analyzer is provided with patient samples that can be randomly accessed in trays that are independently moved within the analyzer.

Another advantageous feature of the invention is that a more compact supply of patient sample is provided, by means that are independent of the supply of disposable tips.

Other advantageous features will become apparent upon reference to the following Discription of the Preferred Embodiments, when read in light of the attached drawings.

DESCIPTION OF THE PREFERRED EMBODIMENTS

This invention is described particularly in connection with an analyzer that dispenses patient liquid onto a dried test element in which reagents are preincorporated. In adition, it can be used in an analyzer that tests for analytes using a liquid medium, in a cuvette, or using any other test environment.

Directions such as "up", "down", "under" and "bottom" as used herein refer to the orientations of the parts as used in their normal operation.

Figure 1:
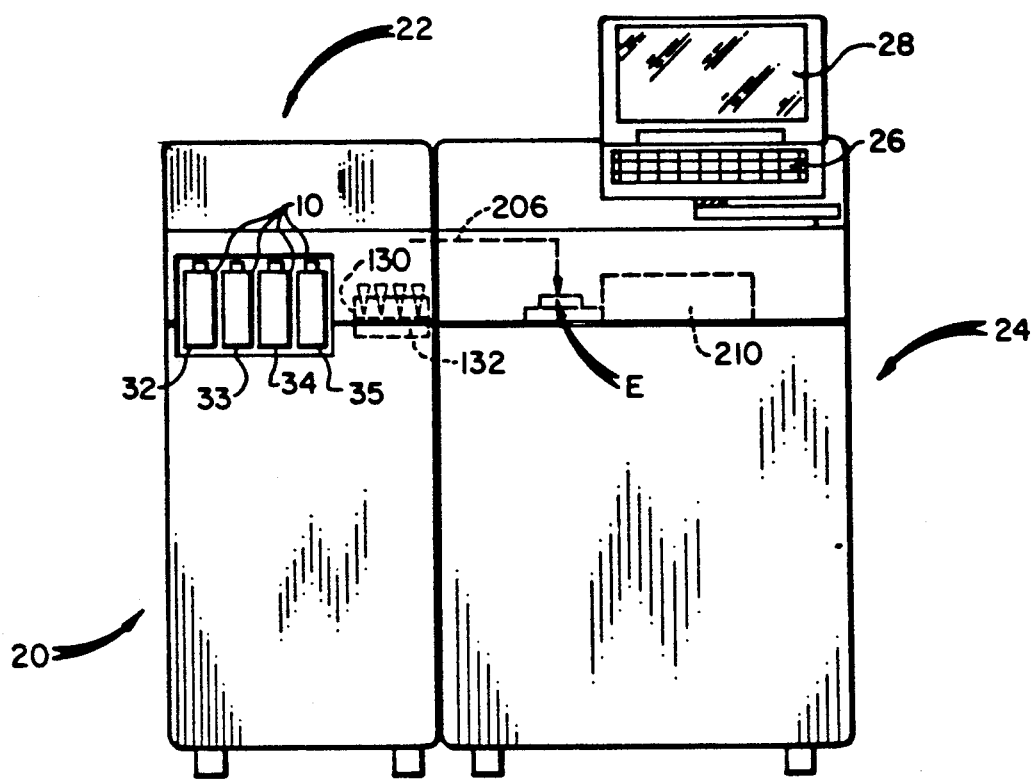
FIG. 1 is a front elevational view of an analyzer constructed in accordance with the invention.
Figure 2:
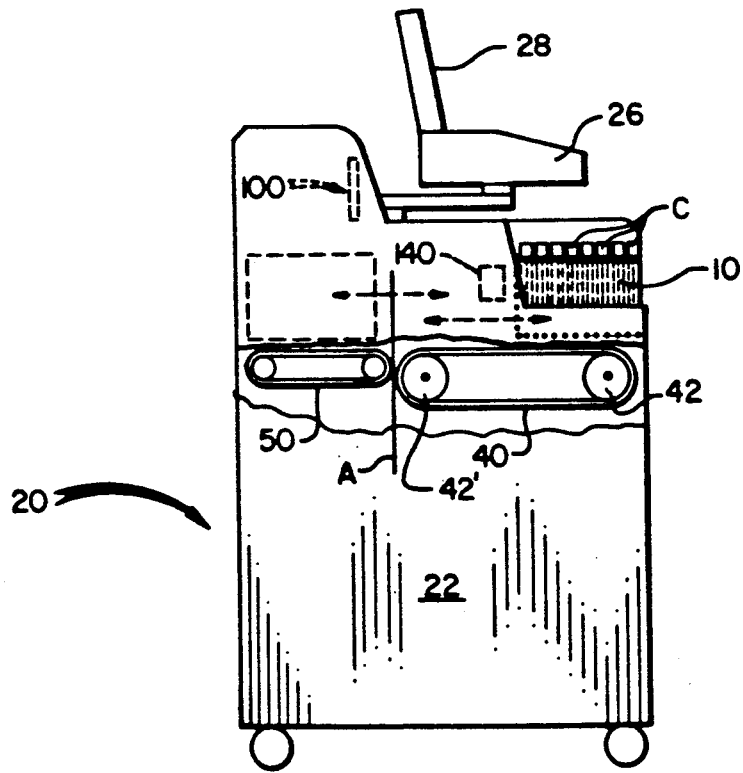
FIG. 2 is a side elevational view, partially broken away, of the analyzer of FIG. 1.

Preferably, FIGS. 1 and 2, an analyzer 20 constructed in accordance with the invention comprises a patient supply module 22 and a test element module 24. Attached to the analyzer and comprising a part of its I/O capabilities, are a keyboard 26 and a display screen 28, both conventional. The primary function of module 22 is to provide a plurality of patient samples, in containers C mounted in trays 10.

Figure 8B:
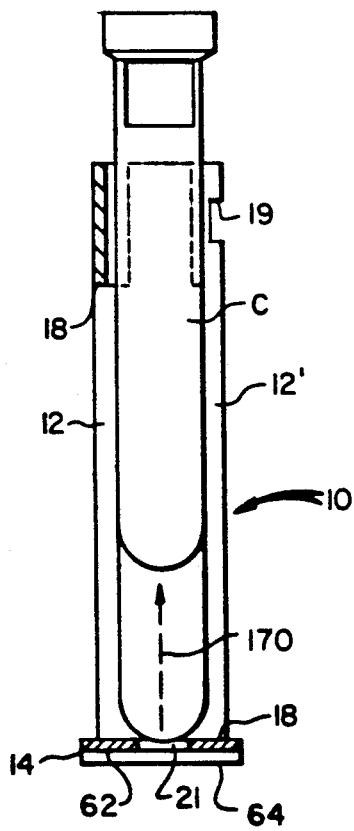
FIG. 8B is an elevational view in transverse section of the tray of FIG. 8A.
Figure 8A:
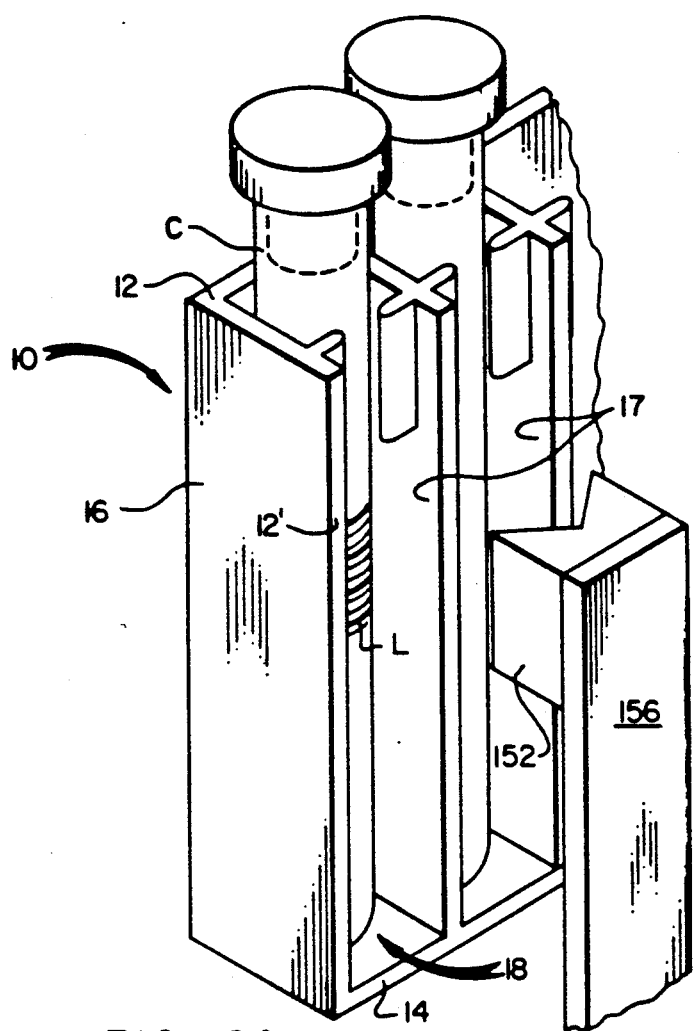
FIG. 8A is a fragmentary perspective view of a tray of the invention.

In accord with one aspect of the invention, trays 10, FIGS. 8A and 8B, comprise two opposed, generally vertical side walls 12, 12', and a bottom wall 14 and end walls 16 connecting these walls. The side walls, by extending the length of the tray, provide the major dimension of the tray and hold the containers in a linear array. Ribs 17, FIG. 8A, separate the containers in the array, and are sized to accommodate a particular sized container. A majority of the surface area of each side wall 12 and 12' is removed, that is is cut out at 18, so as to allow gripping access to a container inside, as described hereinafter. Preferably, a flag 19, FIG. 8B, is provided on a side wall 12 and 12', or another wall of the tray for sensing the location of the tray. A depression 21 (FIG. 8B) in bottom wall 14 aids in seating containers C.

In accord with another aspect of the invention, each of these trays is preferably linear and is mounted in a separate track 32-35 (FIG. 1). Each track has any suitable reciprocating means, such as a conveyor belt 40, FIGS. 2 and 3, mounted on belt wheels 42, 42'. Each belt 40 preferably does not extend the full depth of the analyzer, but rather stops at the plane marked "A", FIG. 2. This is to accommodate a stopper remover, which is optional, discussed below. Belts 40 can be of any convenient construction, such as those that engage trays 10 by friction. In the pairs of belt wheels 42, 42' that drive each belt, one is preferably secured to a drive pulley 44, FIG. 3, driven in a conventional manner such as by a belt or chain 46 and a suitable motor 47 mounted between wheels 42, 42' on a frame member 48, 48', 48", and 48''', respectively.

Figure 3:
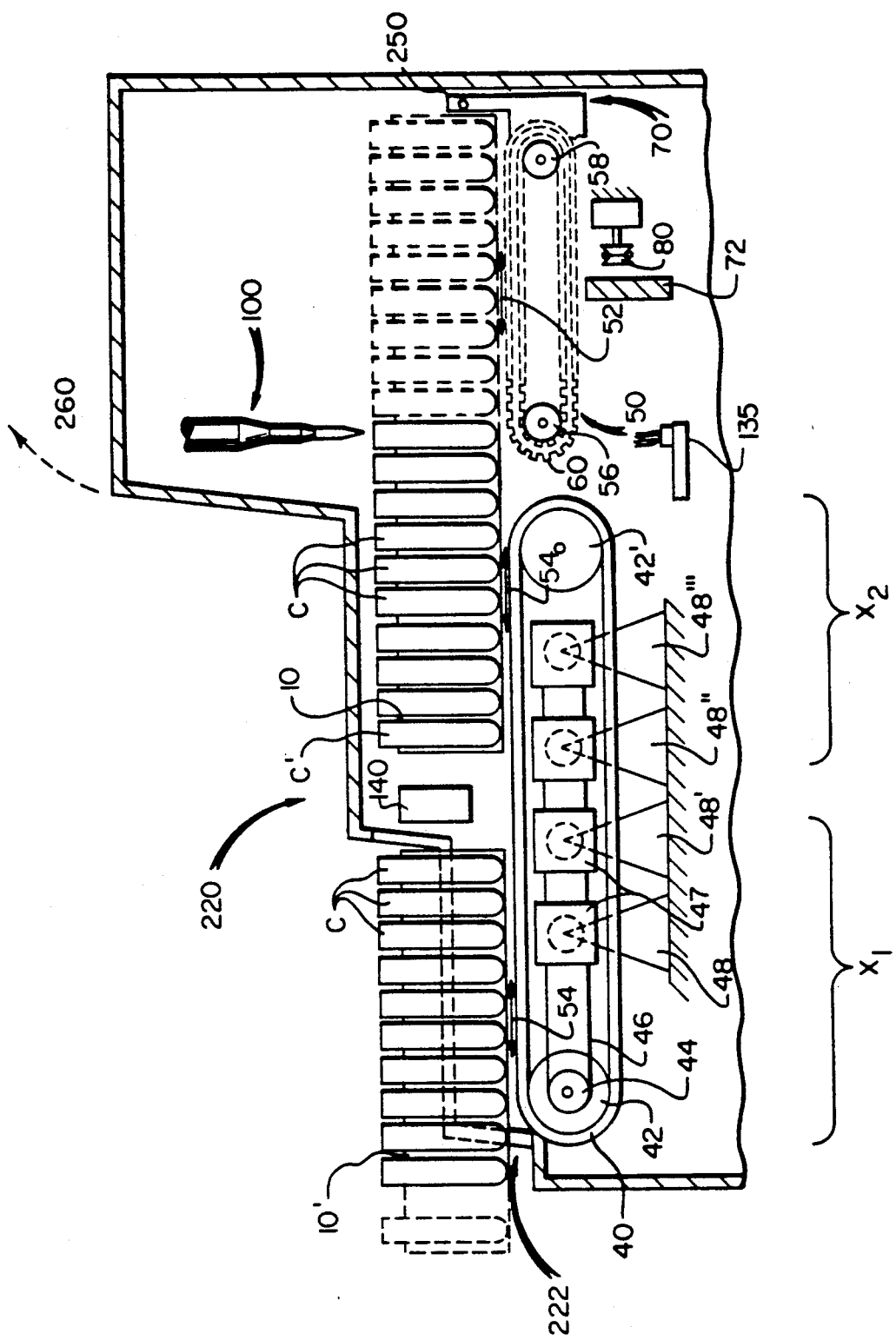
FIG. 3 is a fragmentary elevational view from the side opposite to that of FIG. 2, partially in section.
Figure 4:
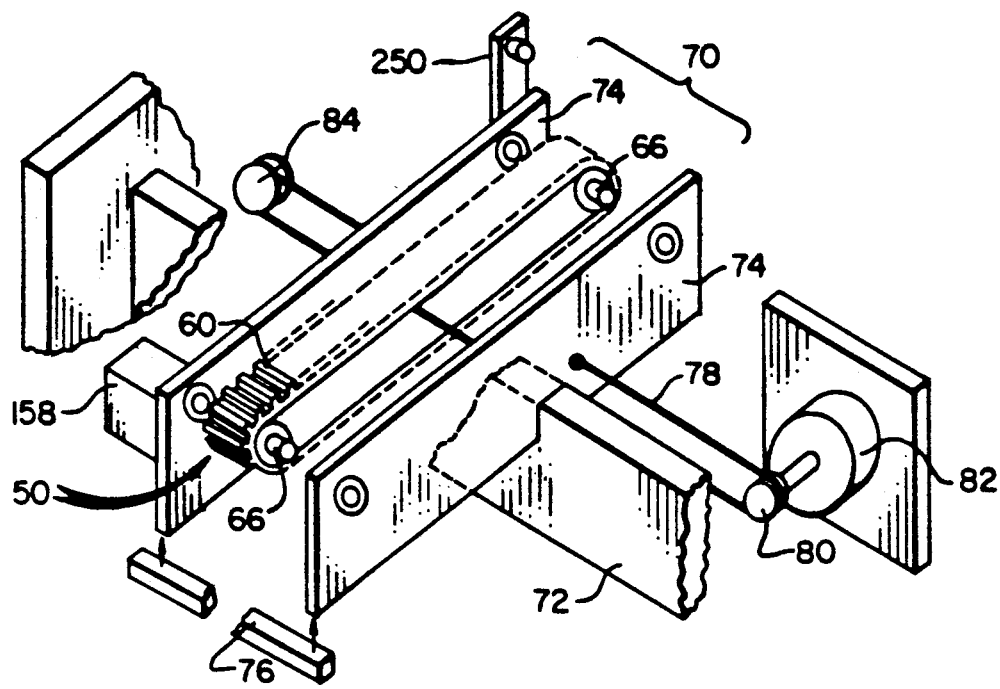
FIG. 4 is a fragmentary perspective view of one of the conveyors of the analyzer, shown exploded in part, for clarity.

To reciprocate each of the trays 10 beyond its track provided by conveyors 40 and beyond plane A, a single conveyor 50 is provided, FIGS. 2 and 3, on a movable cart 70, FIGS. 3 and 4. It is this conveyor that brings a tray and each of its containers into an intersecting position with the path of movement of an aspirating and dispensing station 100, described hereinafter. More specifically, conveyor 50, FIG. 3, is reciprocated for conveying trays in a direction 52 that parallels the conveying directions 54 of conveyor belts 40, by means of belt wheels 56 and 58, one of which is conventionally driven. Most preferably, belt 50 has teeth 60 on both sides thereof. The underside teeth engage the belt wheels, and the upperside teeth engage suitable top lands and grooves in trays 10, to insure positive drive to the tray as it comes from one of the tracks 32-35. See for example grooves 62 and top lands 64 in tray 10 of FIG. 8B.

Because single conveyor 50 is to serve the needs of all the tracks 32-35, conveyor 50 is mounted for movement in a direction transverse (arrow 302, FIG. 4) or perpendicular to direction 52. That is, conveyor 50 and belt wheels 56, 58 are driven on axles 66 that are journalled in cart 70 that rides, via bearings, not shown, on a rail 72, FIG. 4. Rail 72 is fixed in the analyzer so as to be generally perpendicular to tracks 32-35. Cart 70 in turn comprises generally parallel plates 74 held by a crossbar 76 (shown exploded in FIG. 4 for clarity). Each of the plates 74 is connected to an end of a drive cable 78 driven by a drive wheel 80 and motor 82. The front end of cart 70 optionally mounts a stopper remover as described hereinafter, of which only actuating portion 158 is shown in FIG. 4. Wheel 84 is an idler wheel for cable 78.

In this fashion, conveyor 50 is moved into position to convey a tray 10 beyond any of tracks 32-35, that is, beyond the conveyor 40 of such tracks. Movement of cart 70 to such position is coordinated by a microcomputer in the analyzer, not shown, so that conveyor 50 is in place to receive a tray that is to cooperate with the aspirating and dispensing station 100.

Figure 5:
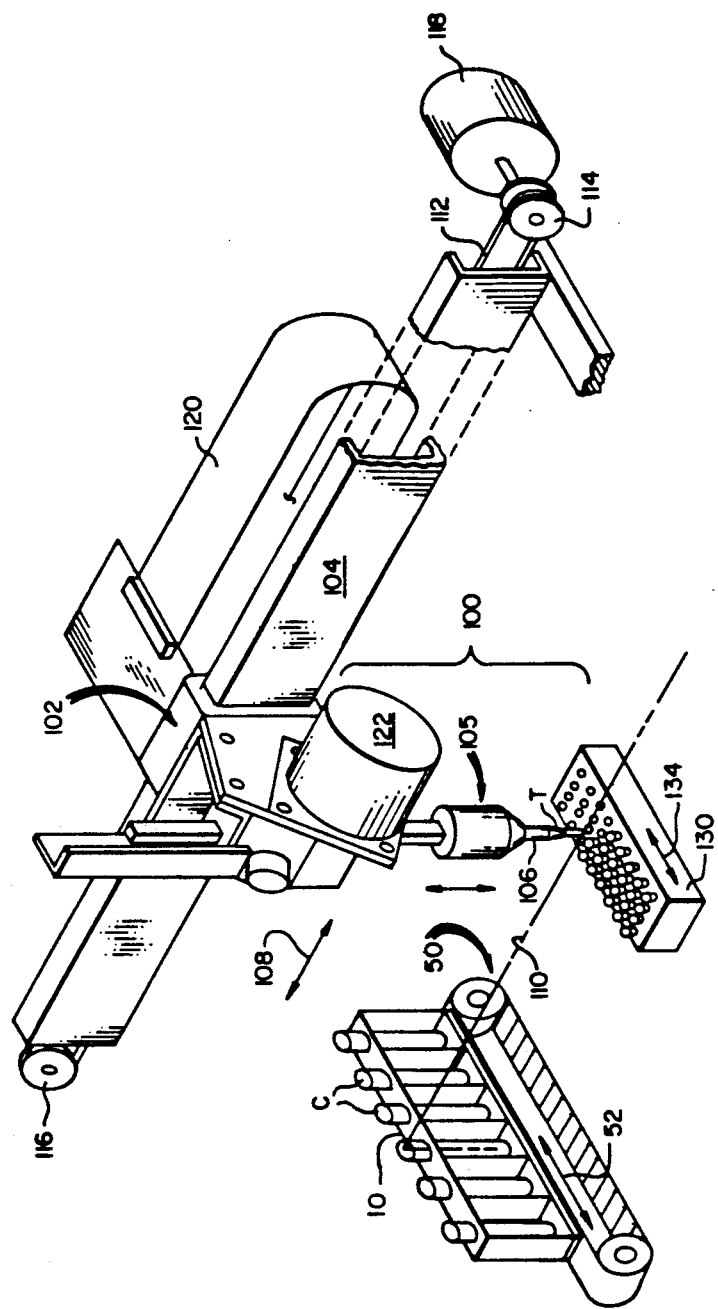
FIG. 5 is a fragmentary perspective view of the mounting of the aspirating and dispensing station.

Station 100, as best seen in FIG. 5, is mounted on a truck 102 that rides via bearings, not shown, on a rail 104 fixed to the analyzer. Truck 102 carries with it a conventional automated aspirating and dispensing pipette 105 of the type described in, e.g., U.S. Pat. Nos. 4,287,155 and 4,340,390, also of the type conventionally found in the analyzer available from Eastman Kodak Company under the trademark "Ektachem 400" ® or "Ektachem 700" ®. Such a pipette has a probe portion 106 designed to removably attach to a disposable tip T, supplied from a rack 130 hereinafter described. Tips T then are inserted into a container C to aspirate liquid into the tip. Accordingly, rail 104 permits truck 102 to reciprocate, arrow 108, along a path 110 that intersects conveyor 50 and a tray 10 positioned thereon, as well as the rack 130, and a test element station (not shown in FIG. 5) described hereinafter. To move truck 102 along path 110, a cable 112 is connected to the truck and is driven by pulley 114 (and idler pulley 116) and motor 118. A suitable card and ribbon cable 120 connect motor 122 of pipette 105 to the microprocessor of the analyzer.

To ensure that enough disposable tips are provided for the patient sample of any tray 10, a rack 130 of tips T is provided, and a conveyor 132, FIG. 1, to move the rack in a direction 134, FIG. 5, generally parallel to conveying direction 52 of conveyor 50. Preferably, sensors such as optical sensors 135, FIG. 3, are provided to ensure that a tip T is present in a particular aperture of rack 130 over which pipette 105 is positioned to descend to pick up a tip, FIG. 5. Rack 130 can be of any convenient construction.

Alternatively, an endless conveyor (not shown) of apertured links can be used, so that an operator continually fills the apertures of the links with tips, at a position outside of the analyzer.

Figure 11:
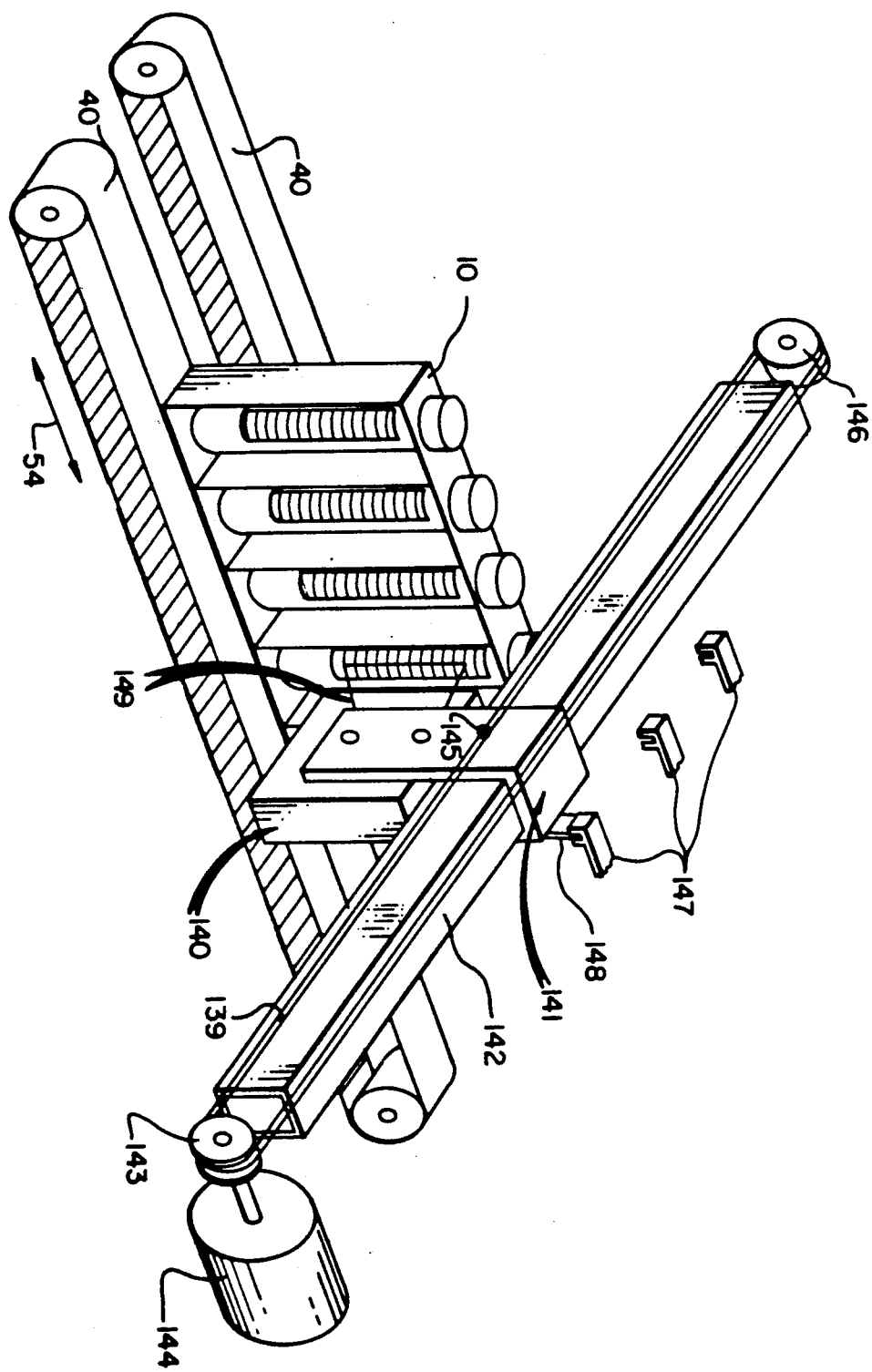
FIG. 11 is a fragmentary perspective view of the driving mechanism for a bar code reader in the analyzer.
Figure 4:
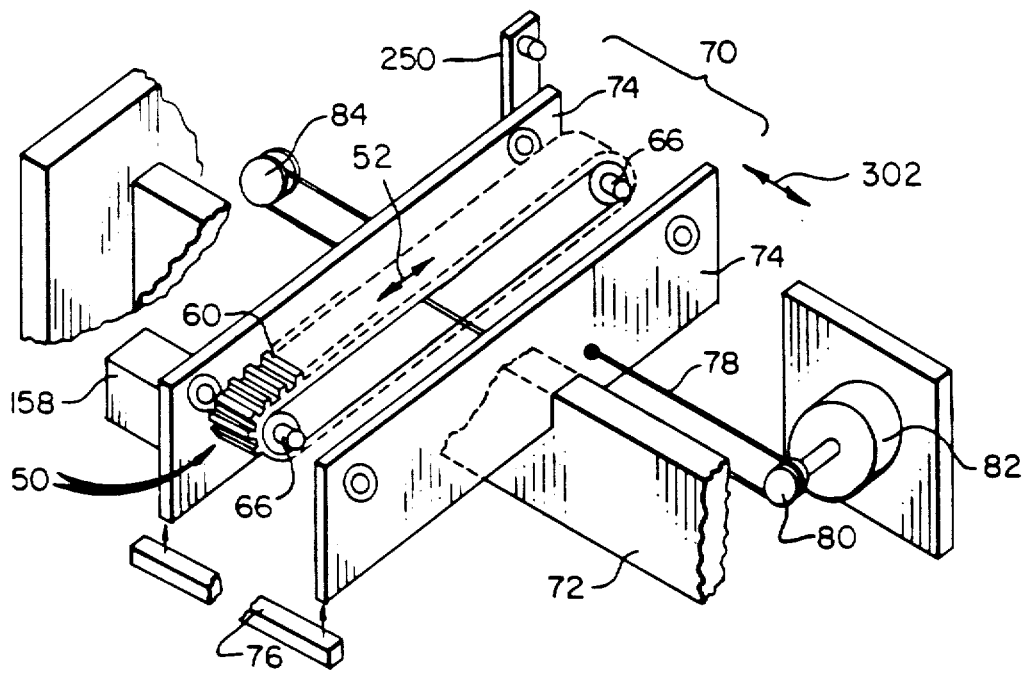

Optionally, and preferably, a bar code reader 140, FIGS. 2 and 3, is mounted for reciprocation to positions closely adjacent any of the tracks 32-35, to read bar code labels L (FIG. 8A) on each container C as the tray on the appropriate track is moved past it. The reader is a conventional reader mounted on a rail and driven by means similar to those provided for station 100. That is, FIG. 11, reader 140 is mounted on a truck 141 that slides over a linear rail 142 on bearings (not shown). Truck 141 is driven by a cable 139, a drive pulley 143 and a drive motor 144. A portion of cable 139 passes above and in front of rail 142 while another portion is fixed to the truck 141 at 145. (An idler pulley 146 completes the drive assembly.) As will be readily apparent, rail 142 extends generally perpendicularly to the direction of movement 54 of belts 40. Sensors 147 are fixed to the analyzer to detect a flag 148 on truck 141 to provide feedback to motor 144. In this manner, movement of truck 141 along rail 142 is halted at the proper position adjacent a belt 40 to allow scanning, using beam 149. After truck 141 is located adjacent the track of the tray to be read, that tray moves from position "$X_1$", FIG. 3, to position "$X_2$". When the last container $C^1$ clears reader 140, the tray 10 is not yet in position to engage conveyor 50 when the latter is moved into alignment with that track.

Figure 6:
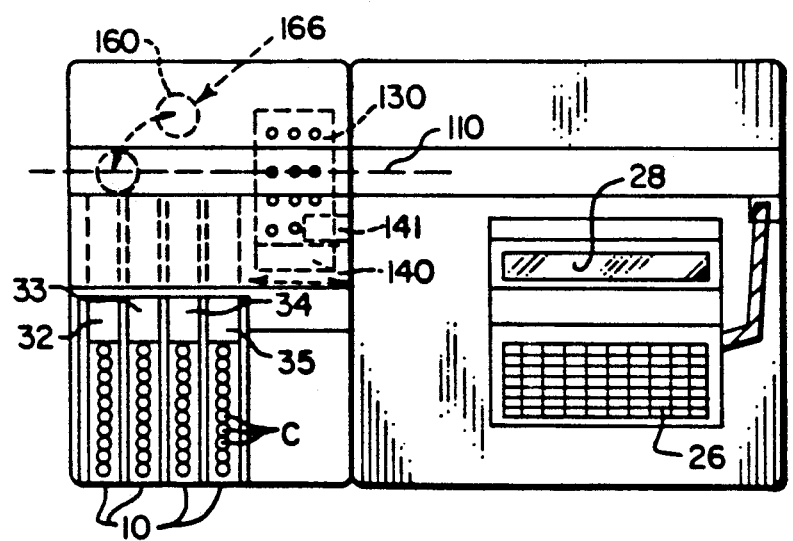
FIG. 6 is a plan view of the analyzer of FIG. 1.
Figure 7:
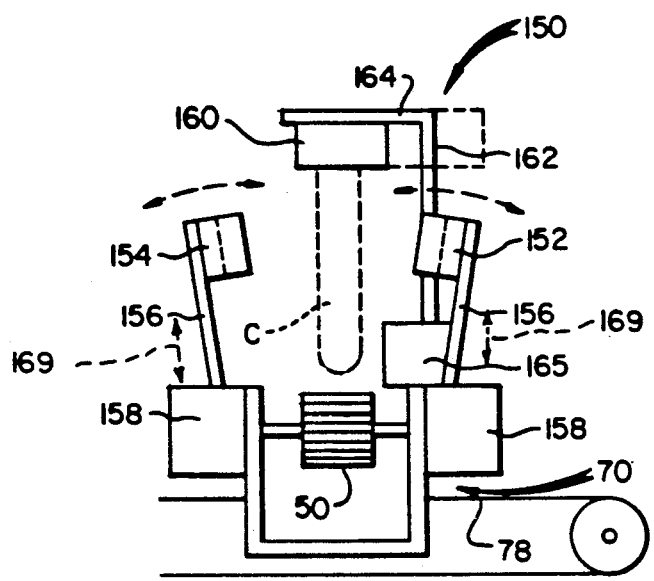
FIG. 7 is a partially schematic, elevational view of the conveyor of FIG. 4, showing also an optional stopper remover.

To allow stoppered containers C to be placed in trays 10, analyzer 20 optionally includes a stopper remover 150 that is carried on cart 70, FIG. 7. Any automated stopper remover is useful, for example, the one described in Japanese Kokai 62/6171. Preferably, such a device includes two tube grippers 152, 154 pivoted on arms 156 via controls 158 mounted on the front of cart 70, and a stopper gripper 160 that includes drive means for removing the stopper (not shown). Most preferably, gripper 160 is mounted on a vertical post 162 and cantelevered arm 164 that pivot via controls 165 so as to move gripper 160 and the removed stopper to a location 166 (shown in phantom, FIG. 7) off path 110, FIG. 6. In this fashion, gripper 160 will not block the movement of truck 102 and pipette 105 as the latter move along path 110 to aspirate from the container that has been unstoppered. Arms 156 also preferably are movable in the direction of arrows 169, FIG. 7, to raise tube C, arrow 170, FIG. 8B, to bring the stopper into engagement with gripper 160. Preferably, both sides 12 and 12' of trays 10 are open to allow grippers 152, 154 to grip an individual tube.

Trays 10 preferably include a flag 19 as described, and another flag, not shown, which is sensed by truck 102 as pipette 105 moves into position for aspiration.

Figure 9:
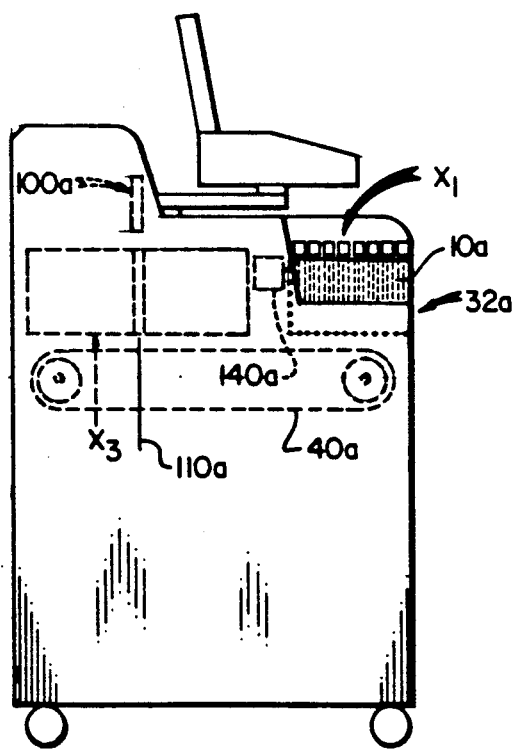
FIG. 9 is an elevational view similar to that of FIG. 2, but of an alternative embodiment.

Alternatively, stopper remover 150 can be dispensed with altogether, as when the containers are placed in trays 10 already unstoppered. That alternative is shown in FIG. 9, in which parts similar to those previously described bear the same reference numeral, to which the distinguishing suffix "a" is appended. In this embodiment, each track 32a-35a (only one being shown) and its conveyor 40a is effective in reciprocating the respective tray 10a to the position ($X_3$) that intersects path 110a of aspirating and dispensing station 100a. That is, second conveyor 50 and its perpendicularly-moving cart 70 are not needed. Bar code reader 140a may or may not be present.

It will be readily apparent from the aforesaid description that a vary compact supply of patient sample is provided, in a manner that encourages more random access than has been heretofore possible. That is, FIG. 3, while a container of tray 10 from track 32 is being aspirated, reader 140 can be reading tray 10 of any one of the other tracks 33-35. If such reader 140 detects that one of the containers of a tray on, for instance track 33 (FIG. 1), has a STAT sample, as soon as aspiration and dispension is completed on the container in progress, tray 10 of track 32 is returned to its track (by conveyor 50 reversing to feed the tray back to conveyor 40 of track 32, also reversed.) Then, tray 10 of track 33 is moved (not shown) onto conveyor 50 (which has been moved into alignment with track 33 from track 32). Conveyor 50 continues to advance this tray until the STAT container intersects path 110. While this is taking place, stopper remover 150 is placed in readiness, and the stopper (if any) is then removed. Gripper 160 is pivoted out of the way, and station 100 is moved into place on path 110 to engage the STAT container.

The aforesaid construction, by providing each tray with its own track extending towards the path of the aspirating and dispensing station, avoids the necessity of moving all the trays lock-step along a path perpendicular to that extending track until a tray lines up with such track.

Figure 10:
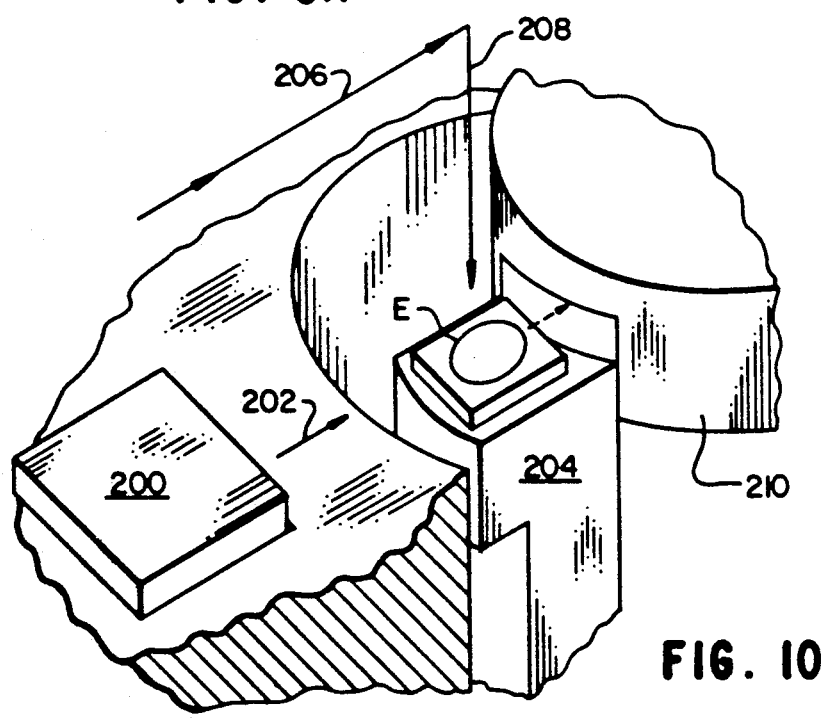
FIG. 10 is a fragmentary perspective view, partly schematic, of the dispensing of liquid onto a test element in the analyzer.

The rest of the operation of the analyzer is conventional, being directed to the dispensing of patient sample onto a test element E, FIG. 10, and the incubating and reading of such an element. Any suitable arrangement can be used for these functions. For example, the following, supplied for completeness, is useful: A supply 200 of elements is provided, and one of such elements E is ejected. arrow 202, onto a platform 204. Station 100 then traverses out of module 22, FIG. 1, into module 24 (arrow 206), and the pipette is moved down (arrow 208, FIG. 10) to a position directly above element E, at which time dispensing occurs. Element E is then conventionally pushed into any suitable incubator 210, and read colorimetrically or potentiometrically at a suitable read station, not shown.

Additional useful features of this invention include:

When any tray 10 is completed with all sample having been aspirated as sensed by sensor 250, FIGS. 3 and 4, on cart 70, conveyor 40 returns it to a protruding position, shown in phantom, FIG. 3, that informs the operator that it can be removed.

A cover 220 (FIG. 3) is provided, which is slotted at 222 so as to expose any tray only when it first enters (or last exits) its track. All trays at station 100 are inaccessible to the operator, thus eliminating the temptation of operators to place STAT containers close to the aspirating and dispensing station. To permit non-routine access to the interior for repairs, such as by the site administrator, cover 220 is held in the position shown by a lock (not shown), and when unlocked, pivots out of its blocking position, arrow 260.

The invention has been described in detail with particular reference to preferred embodiments thereof, but it will be understood that variations and modifications can be effected within the spirit and scope of the invention.

What is claimed is:

1. In an analyzer comprising supply means for supplying patient sample, aspirating and dispensing means for aspirating sample from said supply means and dispensing sample onto a test element, supply means for supplying test elements, and means for moving said aspirating and dispensing means in the analyzer relative to said supply means along a predetermined path and into operative association with said sample and a test element, respectively; the improvement wherein said supply means comprise (a) a plurality of trays each comprising means for holding a plurality of sample containers in a linear array, (b) a separate linear track for each of said trays, in which said trays are mounted, and (c) means for reciprocating each of said trays within its respective track and positioning each of said trays so that each said tray intersects said path of said aspirating and dispensing means.

2. An analyzer as defined in claim 1, wherein said tray-reciprocating means includes (1) sensing means for sensing when the last container of a tray has been aspirated, and (2) means for ejecting said emptied tray at least partially from its respective track to indicate an "empty" condition.

3. An analyzer as defined in claim 1, and further including means for detecting patient identification on said containers in each tray as said each tray is reciprocated along its respective track.

4. An analyzer as defined in claim 3, wherein said detecting means is mounted on a track that passes over said tray tracks, and further including means for moving said detecting means along its track from one tray track to another.

5. An analyzer as defined in claim 4, wherein said track of said detecting means and said path of said aspirating and dispensing means are separate but generally parallel.

6. An analyzer as defined in claim 1, and further including tip supply means comprising a rack of disposable tips separate from said trays, means for moving said rack past said path of said aspirating and dispensing means, and means for sensing a tip in said rack prior to said aspirating and dispensing means moving to association with said tip supply means to pick up said sensed tip.

7. An analyzer as defined in claim 1, wherein said tracks are generally parallel to each other, and said path of said aspirating and dispensing means intersects each of said tracks at an angle of about 90°.

8. An analyzer as defined in claim 1, wherein said reciprocating means include conveyors for each of said tracks, and a separate conveyor mounted so as to (a) convey said trays in a direction that is generally parallel to the direction of conveyance of any of said conveyors, and (b) reciprocate said each tray in a generally perpendicular direction to said parallel directions and along said path of movement of said aspirating and dispensing means; and means for reciprocating said separate conveyor in said perpendicular direction.

9. An analyzer as defined in claim 8, wherein said separate conveyor includes means for interlocking with portions of any of said trays so as to positively drive said trays away from said conveyors of said tracks.

10. An analyzer as defined in claim 1, wherein said rciprocating means comprise first conveyors for each of said tracks and a second conveyor positioned beyond said tracks for conveyance of said trays in a direction parallel to said tracks, means for moving said first conveyors along said tracks, and means for moving said second conveyor transversely to said direction, to a position in which it is alternately aligned with any one of said tracks.

11. An analyzer as defined in claim 1, and further including protective cover means for preventing normal operator access to said aspirating and dispensing means and to at least a portion of said tracks.

* * * * *

UNITED STATES PATENT AND TRADEMARK OFFICE
CERTIFICATE OF CORRECTION

PATENT NO. : 5,008,082

DATED : April 16, 1991

INVENTOR(S) : James D. Shaw

It is certified that error appears in the above-identified patent and that said Letters Patent is hereby corrected as shown below:

IN THE DRAWINGS
   On Sheet 3 of the drawings, replace Fig. 4 with the attached Fig. 4.

Column 3, line 4 should read:   --upon reference to the following Description of the Pre---.

Column 6, line 33 should read:   --dispensing is completed on the container in progress,--.

Column 8, line 13 should read:   --said aspirating and dispensing means moving into associa---.

Signed and Sealed this

Fifth Day of January, 1993

Attest:

DOUGLAS B. COMER

Attesting Officer

Acting Commissioner of Patents and Trademarks